United States Patent
Kauffman et al.

(10) Patent No.: US 7,485,596 B2
(45) Date of Patent: Feb. 3, 2009

(54) PROCESS FOR SYNTHESIZING A HETEROPOLY ACID CATALYST FOR OXIDATION OF UNSATURATED ALDEHYDES TO UNSATURATED CARBOXYLIC ACID

(75) Inventors: James W. Kauffman, Katy, TX (US); Lixia Cai, Maple Glen, PA (US); Wugeng Liang, Katy, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 390 days.

(21) Appl. No.: 11/320,319

(22) Filed: Dec. 28, 2005

(65) Prior Publication Data

US 2007/0149388 A1 Jun. 28, 2007

(51) Int. Cl.
*B01J 27/00* (2006.01)
*B01J 27/198* (2006.01)
*B01J 27/188* (2006.01)
*B01J 27/19* (2006.01)
*B01J 27/192* (2006.01)
*B01J 27/185* (2006.01)
*B01J 23/00* (2006.01)

(52) U.S. Cl. .............. 502/212; 502/208; 502/209; 502/210; 502/211; 502/213; 502/305; 502/308; 502/313; 502/317; 502/319; 502/325; 502/328; 502/330; 502/340; 502/344; 502/349; 502/353; 502/355

(58) Field of Classification Search ......... 502/208–213, 502/305–355
See application file for complete search history.

(56) References Cited

U.S. PATENT DOCUMENTS

| | | | | |
|---|---|---|---|---|
| 3,541,143 A | * | 11/1970 | Nakano et al. | 562/535 |
| 3,998,876 A | * | 12/1976 | Kato et al. | 562/535 |
| 4,388,223 A | * | 6/1983 | Ferlazzo et al. | 502/211 |
| 4,495,109 A | * | 1/1985 | Grasselli et al. | 558/324 |
| 5,198,579 A | * | 3/1993 | Honda et al. | 562/535 |
| 5,206,431 A | | 4/1993 | Hashiba et al. | |
| 5,532,199 A | | 7/1996 | Watanabe et al. | |
| 5,550,095 A | | 8/1996 | Naito et al. | |
| 5,618,974 A | | 4/1997 | Kurimoto et al. | |
| 6,946,422 B2 | * | 9/2005 | Stevenson et al. | 502/311 |
| 7,045,482 B2 | * | 5/2006 | Chun et al. | 502/208 |

OTHER PUBLICATIONS

Concise Chemical and Technical Dictionary ; H. Bennet, Ed.; Third Enlarged Edition; p. 949; Chemical Publishing Co., Inc. (1974).
Concise Chemical and Technical Dictionary; H. Bennet, Ed.; Third Enlarged Edition; p. 964; Chemical Publishing Co., Inc. (1974).
The Merck Index; S. Budavari, Ed.; Twelfth Edition; ; p. 211-213; Merck Research Laboratories (1996).
CRC Handbook of Physics and Chemistry; D. R. Lide, Ed.; p. 4-47; 81st Edition (2000).

* cited by examiner

*Primary Examiner*—J. A. Lorengo
*Assistant Examiner*—Patricia L Hailey
(74) *Attorney, Agent, or Firm*—Jim Wheelington

(57) ABSTRACT

The present invention is for a process for making a heteropoly acid compound catalyst for oxidation of unsaturated aldehydes, such as methacrolein, to unsaturated carboxylic acids, such as methacrylic acid, said catalyst containing oxides of molybdenum, phosphorus, and M', wherein M' is cesium, potassium, rubidium, or sodium, and bismuth. The process is a synthesis of the catalyst with specific process conditions for addition of the bismuth compound as an aqueous slurry without nitric acid. A catalyst precursor is formed by removing the water and drying the solid particles. The heteropoly acid compound catalyst is formed by calcination of the catalyst precursor.

23 Claims, No Drawings

PROCESS FOR SYNTHESIZING A HETEROPOLY ACID CATALYST FOR OXIDATION OF UNSATURATED ALDEHYDES TO UNSATURATED CARBOXYLIC ACID

BACKGROUND OF THE INVENTION

1. Field of the Invention

This invention relates to a method of making heteropoly acid catalyst compositions which can be used in a process for the oxidation of unsaturated aldehydes, such as methacrolein, to unsaturated carboxylic acids, such as methacrylic acid, in a vapor phase reaction.

2. Description of the Prior Art

Heteropoly acid compounds have a central metal atom surrounded by a framework of other metal atoms connected to each other and the central metal atom through oxygen atoms, i.e., metal oxide clusters forming heteropolyoxoanions in acid form. The central metal atom is different ("hetero") from the framework metal atoms. Heteropoly acid compounds can contain oxides of metals such as molybdenum, phosphorus, vanadium, cesium, copper, bismuth, boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum. Heteropoly acid compounds are known as catalysts for the gas phase catalytic oxidation of unsaturated aldehydes to unsaturated carboxylic acids.

U.S. Pat. No. 5,618,974 discloses production of methacrylic acid by the vapor-phase oxidation and/or oxidative dehydrogenation of methacrolein, isobutyl aldehyde or isobutyric acid with a catalyst of a heteropoly acid component of a composite oxide of molybdenum and phosphorus and a solid acid component having acid strength of not more than −11.93. Example 23 discloses a solution of ammonium molybdate in water to which phosphoric acid, a solution of cesium nitrate in water, bismuth nitrate and antimony pentoxide in powdery form and a solution of chromic anhydride and selenium dioxide in water were added.

U.S. Pat. No. 5,550,095 discloses a process for synthesis of methacrylic acid from methacrolein with a solid catalyst obtained from extrusion molding a mixture of methyl alcohol, ethyl alcohol, propyl alcohol, butyl alcohol or acetone and the dried heteropoly acid product from an aqueous slurry containing at least molybdenum, phosphorus and vanadium. Example 5 discloses a homogeneous bismuth nitrate solution obtained from heating nitric acid, water and bismuth nitrate added to a solution of ammonium paramolybdate, ammonium metavanadate, potassium nitrate, cesium nitrate, phosphoric acid, arsenic acid, cerium nitrate and copper nitrate. Antimony trioxide was added after the bismuth nitrate solution.

U.S. Pat. No. 5,532,199 discloses a carrier-supported catalyst for the synthesis of unsaturated aldehydes and unsaturated carboxylic acids. The catalyst has at least molybdenum and bismuth as components of a composite oxide and glass fiber as a carrier. Example 1 discloses a solution of nitric acid, water and bismuth to which ferric nitrate, nickel nitrate, cobalt nitrate, magnesium nitrate, zinc nitrate and boric acid were adder to form a solution which was added to a solution of ammonium paramolybdate, ammonium paratungstate, cesium nitrate and antimony trioxide in water.

U.S. Pat. No. 5,206,431 discloses a process for producing methacrylic acid with a plurality of heteropoly catalysts of different activities in a plurality of reaction zones. Example 13, discloses a solution of ammonium paramolybdate and ammonium metavanadate in heated water to which orthophosphoric acid, an aqueous solution of strontium nitrate, and palladium nitrate, powdery bismuth nitrate, powdery ammonium tungstate and an aqueous solution of chromic anhydride and selenium dioxide were added.

SUMMARY OF THE INVENTION

The present invention is for a method of making heteropoly acid catalyst compositions which can be used in a process for the oxidation of unsaturated aldehydes, such as methacrolein, to unsaturated carboxylic acids, such as methacrylic acid, in a vapor phase reaction. The heteropoly acid catalyst composition has the general formula $Mo_{12}P_bM'_cBi_eO_x$ where Mo is molybdenum, P is phosphorus, M' is cesium, potassium, rubidium or sodium, Bi is bismuth and O is oxygen, b is 0.5 to 3.5, c is 0.1 to 1.5, e is 0.0 to 2.0 and x satisfies the valences. One heteropoly acid catalyst composition of the present invention has the general formula $Mo_{12}V_aP_bCs_cCu_dBi_eM_fO_x$ where Mo is molybdenum, V is vanadium, P is phosphorus, Cs is cesium, Cu is copper, Bi is bismuth, M is boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum, O is oxygen, a is 0.01 to 5.0, b is 0.5 to 3.5, c is 0.1 to 1.5, d is 0.0 to 1.5, e is 0.0 to 2.0, f is 0.0 to 5.0, and x satisfied the valences.

In general, the method of making the catalyst is to dissolve compounds of the catalyst components of the heteropoly acid compound, such as molybdenum compounds, phosphorus compounds, and M' compounds, wherein M' is cesium, potassium, rubidium or sodium, in a solution except for the bismuth compound which is mixed with water to form a slurry which is added to the solution, precipitating particles of the catalyst precursor, evaporating the liquid, drying the solid particles and calcining the solid particles. Other compounds, such as vanadium compounds, copper compounds and one of more compounds of boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum may also be added to the solution or to the mixture.

In general, the process of using the catalyst compositions for the oxidation of unsaturated aldehydes to unsaturated carboxylic acids, in a vapor phase reaction is to contact the unsaturated aldehyde, such as methacrolein, with an oxidizing agent, such as air or another oxygen-containing gas, in the presence of the heteropoly acid compound catalyst at conditions to produce an unsaturated carboxylic acid, such as methacrylic acid.

DETAILED DESCRIPTION OF THE INVENTION

Heteropoly acid compounds containing molybdenum, vanadium, phosphorus, cesium, copper and bismuth are effective as catalysts for the oxidation of unsaturated aldehydes, such as methacrolein, to unsaturated carboxylic acids, such as methacrylic acid, in a vapor phase reaction. The presence of bismuth in a heteropoly acid compound can be beneficial for improvement of selectivity to the desired product. Heteropoly acid compounds can be made by dissolving compounds of the catalyst components in a mixture, precipitating particles of the catalyst precursor, drying the solid particles and calcining the solid particles. However, bismuth compounds, such as bismuth nitrate and bismuth oxide, can be difficult to dissolve. Generally, the bismuth compound is dissolved separately in nitric acid and then the solution of the bismuth compound and the nitric acid is added to a solution of the dissolved compounds of other components of the heteropoly acid compound.

The method of the present invention for making a heteropoly acid compound allows for the addition of a slurry of a solid bismuth compound in water to a solution of dissolved compounds of other components of the heteropoly acid compound to form a mixture. Compounds containing the elements of the particular heteropoly acid compound except for the bismuth compound, such as molybdenum compounds, phosphorus compounds and M' compounds, wherein M' is cesium, potassium, rubidium or sodium, are dissolved in a liquid which may be aqueous, aqueous/organic mixtures or organic to form a solution. The liquid is preferably aqueous. The liquid, solution or mixture may be acidified to promote dissolution of the compounds. The acid may be added before the components other than bismuth are added, i.e., to the liquid, after the components other than bismuth are added (and before the bismuth is added), i.e., to the solution, or after the bismuth is added, i.e., to the mixture. The acid may be organic, such as acetic acid, or inorganic, such as nitric acid. The acidity of the liquid, solution or mixture may be completely or partially neutralized by the addition of a base, such as an ammonium-containing compound, e.g. ammonium hydroxide. Dissolution of the compounds may also be promoted by heating, agitating or aging the solution. Precipitation may occur spontaneously as the compounds are mixed together in solution or it may be promoted by heating, cooling or other changes in ambient conditions or by adding a material which will act as a nucleus or "seed" for precipitation of particles. This "seed" material can be a compound containing one or more of the elements of the catalyst composition.

The addition of the bismuth compound is as aqueous slurry which does not contain any acid, particularly nitric acid. A sufficient amount of the bismuth compound is added to water to make an aqueous slurry which is about 15% by weight bismuth compound. Without limiting the claimed invention, it is believed that the bismuth compound and water may react to form a bismuth oxynitrate. The aqueous slurry may be agitated to disperse the bismuth compound by mechanical agitation or sonification.

Other compounds, such as vanadium compounds, copper compounds and one or more compounds of boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum may also be added to the liquid, i.e. with the molybdenum compound, the phosphorus compound and the M' compound, wherein M' is cesium, potassium, rubidium or sodium, to the mixture, i.e., after the aqueous slurry of the bismuth compound has been added to the solution to form a mixture, or after precipitation. These compounds may be added as solids, solutions or slurries.

Suitable molybdenum compounds are, but not limited to, ammonium paramolybdate, molybdenum trioxide, molybdenum chloride or mixtures or combinations thereof.

Suitable phosphorus compounds are, but not limited to, phosphoric acid, ammonium phosphite or mixtures or combinations thereof.

Suitable M' compounds, wherein M' is cesium, potassium, rubidium or sodium, are, but not limited to, nitrates, oxides, chlorides, or mixtures or combinations thereof.

Suitable copper compounds are, but not limited to, copper nitrate, copper chloride or mixtures or combinations thereof.

Suitable bismuth compounds are, but not limited to, bismuth nitrate, bismuth oxide, bismuth chloride or mixtures or combinations thereof.

Suitable vanadium compounds are, but not limited to, ammonioum, metavanadate, vanadium pentoxide, vanadium chloride or mixtures or combinations thereof.

Suitable boron compounds are, but are not limited to, boric acid, boric hydroxide and boron oxide.

Suitable antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum compounds are, but not limited to, nitrates, oxides, chlorides or mixtures or combinations thereof. Antimony oxide may be added as a solid after the aqueous slurry of the bismuth compound is added to the solution to form a mixture or after precipitation.

The mixture of compounds may be aged for 2 to 24 hours, preferably 1 to 10 hours, most preferably 0.1 to 5 hours. The liquid of the mixture may be removed by evaporation to leave a solid precipitate which may be dried and calcined to obtain a catalyst. The liquid may be evaporated at a temperature of 50° to 125° C. The liquid of the mixture may be removed and the solid precipitate dried at the same time by spray drying.

Drying of the catalyst precursor may be in air or an inert gas and in an oven, a spray dryer or other suitable drying equipment as known in the art. Preferably, drying is in an oven in air at a temperature of 100-150° C. for 2-5 hours One purpose of calcination of the catalyst precursor is to activate the catalyst by obtaining an oxide of the metal components. The catalyst precursor may be calcined at a temperature of above about 350° C. for about 2 to about 12 hours. The calcination may be in two stages, one at a temperature lower than about 350° C. for about 1 to about 8 hours and another at a temperature above 350° C. for about 2 to about 12 hours. Calcination may be done in a high temperature oven or kiln. Calcination can also drive off water, present as absorbed moisture, and other volatile constituents, such as nitrates for the catalyst precursor of the present invention.

The catalyst may be processed by sieving, forming and other means known in the art to obtain catalyst particles of a certain size. Desired particle size and particle size distribution are related to the design of the reactor (size, shape, configuration, etc.), to the pressure drop intended for the process and to the process flow.

The process of oxidation of unsaturated aldehydes, such as methacrolein, to unsaturated carboxylic acids, such as methacrylic acid, in a vapor phase reaction using a heteropoly acid compound as a catalyst is to contact the unsaturated aldehyde with an oxidizing agent in the presence of the heteropoly acid compound catalyst at reaction conditions to produce an unsaturated carboxylic acid.

The feedstock for this process may contain, in addition to unsaturated aldehydes, water, carbon monoxide, carbon dioxide, acetone, acetic acid, acrolein, methacrylic acid, olefins and other saturated and unsaturated hydrocarbons. The concentration of unsaturated aldehydes may vary over a wide range. In one embodiment of the present invention, the concentration of unsaturated aldehydes for the process is from about 1 vol. % to about 20 vol. %, preferably from about 2 vol. % to about 8 vol. %, of methacrolein.

The oxidizing agent may be air or another oxygen-containing gas. There may be gases or vapors other than oxygen, such as nitrogen, carbon dioxide, noble gases and steam, in the oxidizing agent. The oxidizing agent may be pure oxygen. In one embodiment of the process of the present invention, the amount of oxygen relative to aldehyde would be from 40% less than stoichiometric to 700% more than stoichiometric by mole, preferably 60% more than stoichiometric to 360% more than stoichiometric by mole. In another embodiment of the process of the present invention in which the aldehyde is methacrolein, the amount of oxygen relative to methacrolein is from about 0.3 to about 4, preferably from about 0.8 to about 2.3 by mole ratio.

The process conditions are at a pressure from about 0 atm to about 5 atm, preferably at about 1 atm, and at a temperature from about 230° C. to about 450° C., preferably about 250° C. to about 400° C., more preferably about 250° C. to about 350° C.

The reactor for the process of the present invention may be any reactor for a vapor phase reaction, such as a fixed bed reactor, a fluidized bed reactor or a moving bed reactor.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 46.51 g of ammonium paramolybdate and 1.29 g of ammonium metavanadate were dissolved in about 200 ml of deionized water overnight. The following morning 4.28 g of cesium nitrate dissolved in 25 ml of water and 3.80 g of phosphoric acid dissolved in 6 ml of water were added to the molybdate solution at room temperature. 0.51 g of copper nitrate was added to the solution about three minutes later. 5.32 g of solid bismuth nitrate was reacted with 30 ml of water to form a slurry which was added to the solution. The solid bismuth nitrate hydrate immediately started hydrolyzing to form what was believed to be water insoluble bismuth oxynitrate. Heat was then applied to the solution to raise the temperature gradually to about 95° C. over about 50 minutes after which 2.56 g of solid antimony trioxide and 0.68 g of solid boric acid were added to the solution. After about a 30 minutes digestion time, the slurry was boiled down at a temperature of 80-100° C. over 2.3 hours to a moist paste. The paste was dried at about 120° C. for 16 hours. The dried cake was ground to a fine powder, pressed at 10,000 psi and sized to −20+30 mesh. The sized catalyst precursor was calcined at 380° C. for 5 hours with a 0.5° C./min ramp rate.

Comparative Example 1

The same preparation as in the Example was used except for the following: 5.32 g of solid bismuth nitrate hydrate was then added all at once to the solution instead of reacting solid bismuth nitrate with 30 ml of water to form a slurry. After addition of the solid bismuth nitrate hydrate, 4.31 g of concentrated nitric acid dissolved in 30 ml of water was added to the solution.

Comparative Example 2

The same preparation as in Comparative Example 1 was used except for the following: 5.32 g of solid bismuth nitrate was dissolved in 4.3 g of nitric acid diluted in 30 ml of water to form a solution, the bismuth nitrate solution was then added and no additional nitric acid was added after the bismuth nitrate solution.

Comparative Example 3

The same preparation as in Comparative Example 1 was used except for the following: no nitric acid was added after the addition of the solid bismuth nitrate.

For each of the above Example and Comparative Examples, 6.0 cc of the calcined material was loaded in the reactor with 9 cc of quartz chips and the reaction is carried out at 15 psia with a vapor steam of the following composition: 4 vol % methacrolein, 8 vol % oxygen and 30 vol % steam with the balance being nitrogen. Relative activity for the Examples and Comparative Examples are shown in Table I. The activity of a catalyst following the procedure of Comparative Example 2 ("standard catalyst") was defined as 1.0. The absolute percent difference between the activities of the catalysts of the Example and the Comparative Examples and the activity of the standard catalyst is reported in Table I as "relative activity." If the catalyst showed an activity 30% higher than the standard catalyst, then this catalyst would have a relative activity of 1.3.

TABLE I

|  | Relative Activity |
| --- | --- |
| Example | 2.0 |
| Comparative Example 1 | 1.2 |
| Comparative Example 2 | 1.0 |
| Comparative Example 3 | 1.4 |

As can be seen from the Example and the Comparative Examples above, addition of bismuth nitrate as an aqueous slurry to the solution of other compounds (Example) results in improved activity of the catalyst for oxidation of methacrolein to methacrylic acid over a catalyst in which the bismuth nitrate was added as a solid (Comparative Examples 1 and 3) or was dissolved in nitric acid before addition to the solution of other compounds (Comparative Example 2).

As noted above, during calcination volatiles such as nitrates are evolved. The weight loss based on the amount of nitrates and ammonia (metal nitrates, ammonium metal salts, ammonium hydroxides and nitric acid) added as reagents to the reaction slurry can be calculated, assuming that the metal salts are converted to the corresponding metal oxides and all of the ammonia and nitrates are evolved. A predicted value based on the calculated difference between the initial total dry weight of the metal salts, nitric acid salt and ammonium salt before calcination and the calculated combined dry weight of the metal oxides after calcination was calculated for each of the Example and Comparative Examples as shown in Table II. The actual weight loss is based on thermogravimetric analysis of the dry sample. The weight loss from room temperature up to 150° C. is assumed to be moisture loss from the sample. The weight loss from the sample dried at 150° C. up to 270° C. was then assumed to be ammonium nitrate weight loss as shown in Table II.

TABLE II

| Example | Actual $NH_4NO_3$ % Weight Loss RT-270° C. | Predicted $NH_4NO_3$ % Weight Loss RT-270° C. |
| --- | --- | --- |
| Example | 12.4 | 13.6 |
| Comparative Example 1 | 15.9 | 17.8 |
| Comparative Example 2 | 15.9 | 17.8 |
| Comparative Example 3 | 12.8 | 13.6 |

A benefit of the bismuth nitrate addition as an aqueous slurry is that no nitric acid is required. As a result, the weight loss of nitrates during calcination of the catalyst precursor to form the catalyst is significantly less. For example, every 100 tons of catalyst precursor manufactured, there could be a reduction of 0.4 to 3.5 tons or more of ammonium nitrate over other synthesis methods. This is a significant advantage during commercial processing when handling large amounts of catalyst and large amounts of ammonium nitrate salt. The ammonium nitrate salt has to be removed from the product and the resulting emissions captured and disposed of. Significantly reducing the salt content would significantly lower the emissions during processing. An additional benefit is that by lowering the ammonium nitrate content, the possibilities are reduced that the catalyst will be exposed to a destructive exotherm when the ammonium nitrate thermally decomposes. The ammonium nitrate thermally decomposes when the catalyst precursor is heated during the manufacturing process and if heated to too high of a temperature the ammonium nitrate will decompose very rapidly producing an exotherm that will destroy the catalyst.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A process of preparing a heteropoly acid catalyst comprising:
   a) mixing a molybdenum compound, a phosphorus compound and a M' compound into a liquid to form a solution wherein M' is cesium, potassium, rubidium, or sodium;
   b) adding a bismuth compound as an aqueous slurry in the absence of an acid to the solution to form a mixture;
   c) precipitating solid particles;
   d) evaporating liquid to leave solid particles;
   e) drying the solid particles; and
   f) calcining the solid particles to form a heteropoly acid catalyst.

2. The process of claim 1 wherein the molybdenum compound is ammonium paramolybdate, molybdenum trioxide, molybdenum chloride or mixtures or combinations thereof.

3. The process of claim 1 wherein the phosphorus compound is phosphoric acid, ammonium phosphite or mixtures or combinations thereof.

4. The process of claim 1 wherein the M' compound is a nitrate, oxide, chloride or mixtures or combinations thereof.

5. The process of claim 1 wherein the bismuth compound is bismuth nitrate, bismuth oxide, bismuth chloride or mixtures or combinations thereof.

6. The process of claim 1 further comprising the absence of nitric acid.

7. The process of claim 1 wherein further comprising adding a copper compound to the liquid.

8. The process of claim 7 wherein the copper compound is copper nitrate, copper chloride or mixtures or combinations thereof.

9. The process of claim 1 wherein further comprising adding a vanadium compound to the liquid.

10. The process of claim 9 wherein the vanadium compound is ammonium metavanadate, vanadium pentoxide, vanadium chloride or mixtures or combinations thereof.

11. The process of claim 1 wherein further comprising adding one or more compounds of boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum to the liquid.

12. The process of claim 11 wherein the compound of boron is boric acid, boron hydroxide or boron oxide.

13. The process of claim 11 wherein the compound of antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium or lanthanum is a nitrate, oxide, chloride or a mixture or combination thereof.

14. The process of claim 1 wherein the heteropoly acid catalyst has the general formula $$Mo_{12}V_aP_bCs_cCu_dBi_eM_fO_x$$

where Mo is molybdenum, V is vanadium, P is phosphorus, Cs is cesium, Cu is copper, Bi is bismuth, M is boron, antimony, tungsten, cerium, niobium, indium, iron, chromium, cobalt, nickel, manganese, arsenic, silver, zinc, lead, tin, titanium, aluminum, silicon, tantalum, germanium, gallium, zirconium, magnesium, barium and lanthanum, O is oxygen, a is 0.01 to 5.0, b is 0.5 to 3.5, c is 0.1 to 1.5, d is 0.0 to 1.5, e is 0.0 to 2.0, f is 0.0 to 5.0, and x satisfied the valences.

15. The process of claim 1 wherein the mixture is aged for 2 to 24 hours.

16. The process of claim 15 wherein the mixture is aged 1 to 10 hours.

17. The process of claim 16 wherein the mixture is aged 0.1 to 5 hours.

18. The process of claim 1 wherein evaporating is at a temperature of 50° to 125° C.

19. The process of claim 1 wherein evaporating and drying is at the same time by spray drying.

20. The process of claim 1 wherein drying is in air or an inert gas.

21. The process of claim 20 wherein drying is in air at a temperature of 100-150° C. for 2-5 hours.

22. The process of claim 1 wherein calcining is at a temperature of above about 350° C. for about 2 to about 12 hours.

23. The process of claim 22 wherein the calcining is two stages, one at a temperature lower than about 350° C. for about 1 to about 8 hours and another at a temperature above 350° C. for about 2 to about 12 hours.

* * * * *